US 6,560,342 B2

(12) United States Patent
Kang

(10) Patent No.: US 6,560,342 B2
(45) Date of Patent: May 6, 2003

(54) SMART FOAM FOR ACTIVE NOISE CONTROL IN A DUCT AND DEVICE EQUIPPED WITH THE SAME

(76) Inventor: Yoen June Kang, 601-903, Moojigaemaeul, 255, Kumi-dong, Pundang-gu, Seongnam-si, Kyonggi-do (KR)

( * ) Notice: Subject to any disclaimer, the term of this patent is extended or adjusted under 35 U.S.C. 154(b) by 0 days.

(21) Appl. No.: 09/920,731

(22) Filed: Aug. 3, 2001

(65) Prior Publication Data

US 2002/0181715 A1 Dec. 5, 2002

(30) Foreign Application Priority Data

Apr. 13, 2001 (KR) .......................................... 2001-19751

(51) Int. Cl.[7] .......................... A61F 11/06; G10K 11/16; H03B 29/00
(52) U.S. Cl. ...................................... 381/71.5; 381/71.7
(58) Field of Search ............................... 381/71.5, 71.7; 181/222, 224

(56) References Cited

U.S. PATENT DOCUMENTS 6,383,317 B1 * 5/2002 Bellus et al. ............... 181/224

* cited by examiner

Primary Examiner—Minsun Oh Harvey
(74) Attorney, Agent, or Firm—Browdy and Neimark, P.L.L.C.

(57) ABSTRACT

The present invention relates to a smart foam for active noise control in a duct and a device equipped with the same. In particular, the smart foam for the active noise control in a duct according to the present invention comprises: an external ring (52) made out of an elastic porous synthetic resin foam material of a certain length; an internal ring (54) made out of an elastic porous synthetic resin foam to be inserted into the said external ring (52); a ring type PVDF film (60) to be interposed between the said external ring (52) and the internal ring (54) for the radiation of sounds, on the outer and inner surfaces of which film conductive material layers are plated; and lead wires (64) connecting the conductive material layers (62) on the outer and inner surfaces of the said PVDF film (60) to different electrodes and conveying voltages thereto in order to enable the PVDF film (60) to radiate sounds. Therefore, the smart foam for active noise control in a duct according to the present invention may overcome the drawback of the passive noise control by the conventional elastic porous materials. Furthermore, the present invention, which provides a ring type smart foam, made of the ring type elastic porous synthetic resin foam with a hole in the center containing a PVDF actuator embedded inside, may be installed in a duct with the actual movements of fluid and may achieve the enhanced noise control performance.

4 Claims, 10 Drawing Sheets

(a):300Hz,(b):400Hz,(c):750Hz,(d):1500Hz
○:Before control,✳:Foam,△:After the control using the smart foam (a):600±50Hz,(b):900±100Hz ○:Before control,✻:Foam,△:After the control using the smart foam (a):300Hz,(b):400Hz,(c):750Hz,(d):1500Hz
✳:Foam,△:After the control using the smart foam (a): 500 ± 50Hz, (b): 900 ± 100Hz
✳:Foam, △:After the control using the smart foam

SMART FOAM FOR ACTIVE NOISE CONTROL IN A DUCT AND DEVICE EQUIPPED WITH THE SAME

BACKGROUND OF THE INVENTION

1. Field of the Invention

The present invention relates to the smart foam for active noise control in a duct. In particular, the present invention relates to the smart foam for active noise control in a duct which may be easily installed in ring type tubes and which can improve the noise control performance within a duct with fluid's movements.

2. Description of the Related Art

As the noise issue becomes important, the noise problem within ducts used in various machinery and equipment is becoming important increasingly. Until now, the noise in ducts has been controlled by applying noise cut-off materials or absorbing materials, or by attaching devices such as a resonator. While the cut-off material or absorbing material may decrease the noise throughout a broad bandwidth of frequencies, such material may decrease only a limited extent of noise at a low frequency area. On the other hand, the resonator may control only the noise of a certain limited frequencies.

Generally, elastic porous materials reduce noise by dissipating the energy of the incident sound wave, using the friction related to the coupling of the solid constituting the frame and the fluid (air) in the holes. The method of passive noise control using the elastic porous material is the method to absorb sounds merely by installing the elastic porous material between the noise origin and the sound receipt point. This method is simple in structure and easy to implement. Thus, this method has been widely used because of the low cost incurred in installing the device and the broad frequency bandwidth in which noise may be reduced. However, this method has a drawback in that it can hardly control noises of low frequencies.

Accordingly, it was required to develop a new method for noise control and thus the active noise control (ANC) has been studied. Paul Lueg of Germany proposed the basic principle of the active noise control in 1936. Basically, this method reduces noise by generating the control sound, which has the same magnitude as the noise to be controlled and the phase difference of 180 degree from the noise.

For such active noise control, an origin for the control sound is required. Speakers are frequently used for such purpose. However, in order to attach a speaker, the shape of duct must be changed or a portion of the duct must be set aside as a space for the speaker.

In order to resolve such problems, Fuller suggested a smart foam which may generate the control sound. Such smart foam may be created by inserting polyvinylidene fluoride film (PVDF film) inside of the conventional elastic porous foam. The embedded PVDF film serves as an actuator to generate the control sound. The sound is generated by the changes caused upon the fluid and solid of the elastic porous foam. Thus, the smart foam has the advantages of both the passive noise control and the active noise control of the conventional elastic porous material.

FIG. 1 and FIG. 2 illustrate the structure of the smart foam proposed by Fuller.

As illustrated in the drawing, Fuller's smart foam ("Plug type smart foam") has wavy surfaces (12)(22) of the continuous semicircles on the surfaces of the upper foam (10) and the lower foam (20), facing each other. The upper and lower foams are made out of the elastic porous synthetic resin foam. A PVDF actuator (30), which may radiate sounds, is interposed in between the said wavy surfaces (12)(22) and fixed by the means such as an adhesive.

The said PVDF actuator (30) is made of a wavy PVDF film (32), on both surfaces of which conductive materials (34) such as the silver (Ag) are coated. The said conductive material (34) is peeled off through the lines (36) between two semicircles of the said wavy PVDF film, for the effect of the electric insulator. Thus, the said conductive material (34) is composed of four different and independent cells.

By interposing the semicircular PVDF actuator (30) in the elastic porous material composed of the upper and lower foam parts (10)(20) and applying to the neighboring cells the voltage in the opposite directions, the above-described plug type smart foam enables sounds to be radiated as they are radiated from speakers. Thus, in the low frequency level, the active noise control through the PVDF actuator (30) is possible and in the high frequency level, the passive noise control through the elastic porous material is made passable. However, as shown in the drawing, the plug type smart foam is in the form blocking the cross section of a duct. Thus, it may not be applied to control the noise in a duct with the movement of actual fluid. Moreover, unless both ends are baffled, the sound would radiate as the dipole does. Therefore, the sound radiation efficiency decreases abruptly in the free field.

SUMMARY OF THE INVENTION

The purpose of the present invention is to provide the smart foam for active noise control. In particular, the present invention provides the ring type smart form made by inserting a PVDF actuator in the lining shaped ring type elastic porous foam with a hole in the center, which may thus be used in a duct with the movement of fluid inside for the active and passive noise control. Furthermore, the present invention's smart foam radiates sounds in the manner similar to the monopole does even without baffles. Consequently, the present invention provides the smart foam for active noise control with high sound radiation efficiency even in the free field.

Another purpose of the present invention is to provide a device equipped with the smart foam for active noise control in a duct, in the structure enabling the said ring type smart foam to be easily installed within a ring type duct.

In order to achieve the above-mentioned purposes, the present invention's smart foam for active noise control in a duct comprises: an external ring of a certain length, made out of the elastic porous synthetic resin foam; an internal ring made out of the elastic porous synthetic resin foam to be inserted inside of the said external ring; a ring type PVDF film, on both sides of which the conductive materials are coated to radiate sounds and which is to be interposed in between the said external and internal rings; and the lead wire which enables the PVDF film to radiate sounds through the connection of the said PVDF film's inner and outer surfaces to different electrodes and voltages applied to the surfaces.

Furthermore, the device, equipped with the present invention's smart foam for active noise control in a duct, comprises: a ring type smart foam composed of an external ring of a certain length, made out of the elastic porous synthetic resin foam, an internal ring made out of the elastic porous synthetic resin foam to be inserted inside of the said external ring, a ring type PVDF film, on both sides of which the conductive materials are coated to radiate sounds and which is to be interposed in between the said external and internal rings, and lead wires which enable the PVDF film to radiate sounds through the connection of the conductive materials on the said PVDF film's inner and outer surfaces to different electrodes and the voltages applied to the conductive material layers; and a holder composed of the first connection part with a hollow for holding the said ring type smart foam and the second connection part extended from the first connection part, having the smaller inner diameter than the said hollow, to which connection parts (the first and second connection parts) the ducts are connected.

DESCRIPTION OF THE CODES OF IMPORTANT PARTS OF THE DRAWINGS

| 51: | Ring type smart foam | 52: | External ring |
|---|---|---|---|
| 54: | Internal ring | 60: | PVDF film |
| 62: | Conductive material layer | 64: | Lead wire |
| 70: | Holder | 72: | Hollow |
| 74: | First connection part | 76: | Second connection part |
| 78, 80: | Screw parts | | |

DETAILED DESCRIPTION OF THE PREFERRED EMBODIMENTS

Reference will now be made in detail to the preferred implementation of the present invention as illustrated in the accompanying drawings.

Figure 3:
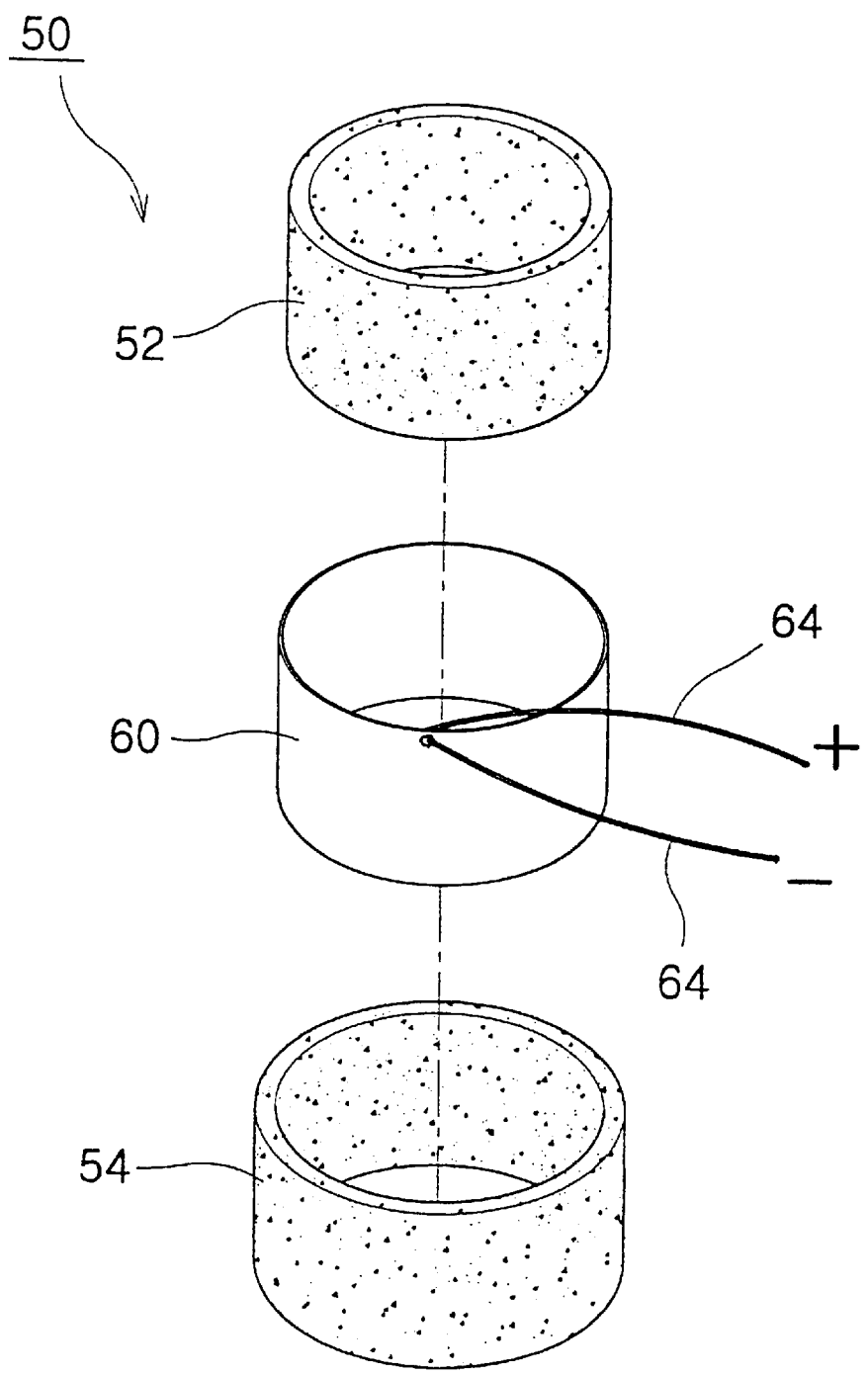
FIG. 3 is a diagram showing the structure of the separated smart foam according to the present invention.
Figure 4:
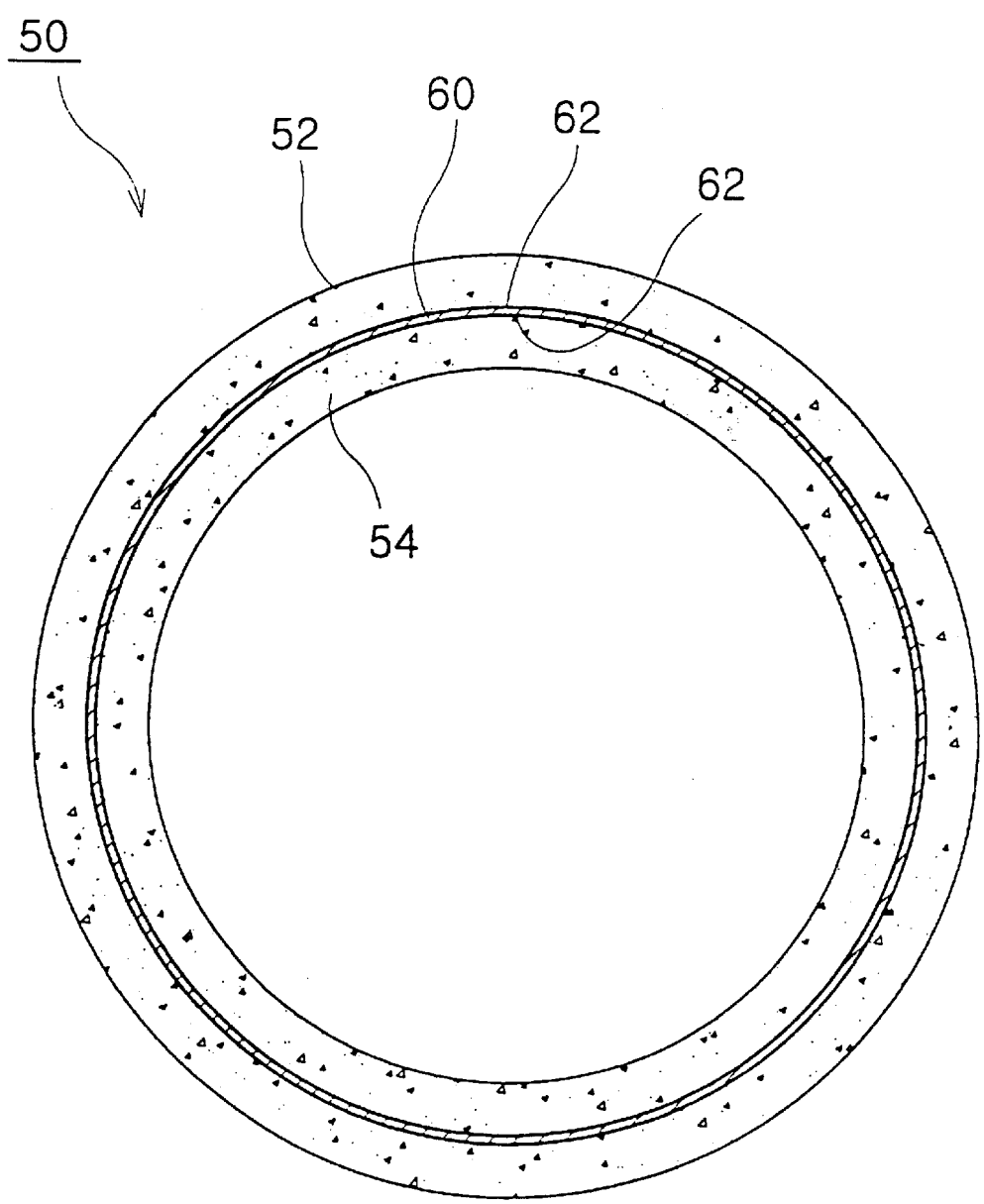
FIG. 4 is a cross sectional view of the smart foam according to the present invention.

FIG. 3 and FIG. 4 illustrate the structure of the smart foam according to the present invention ("Ring Type Smart Foam").

Whereas the sound absorbing/cut-off materials made of synthetic resin foam are conventionally applied to ducts in lining forms, the present invention provides the ring type smart foam with a PVDF film embedded between synthetic resin foams of such lining shape.

As illustrated in the drawing, the ring type smart foam (50) of the present invention comprises: an external ring (52) made out of synthetic resin foam, preferably polyurethane foam, of a certain length; an internal ring (54) made out of synthetic resin foam, preferably polyurethane foam, to be inserted inside of the said external ring (52); a ring type PVDF film (60) to be interposed in between the said external ring (52) and internal ring (54), the inner and outer surfaces of which film are plated with conductive material layers (62), preferably silver (Ag), so that the film may radiate sounds; and lead wire (64) which connects the conductive material layers (62) on the inner and outer surfaces of the said PVDF film (60) to different electrodes and applies voltages, enabling the PVDF actuator (60) to radiate sounds.

According to the present invention, through the connection of the different electrodes to the outer and inner surfaces of the PVDF film (60) in the said ring type smart foam (50), sounds may be radiated.

Figure 5:
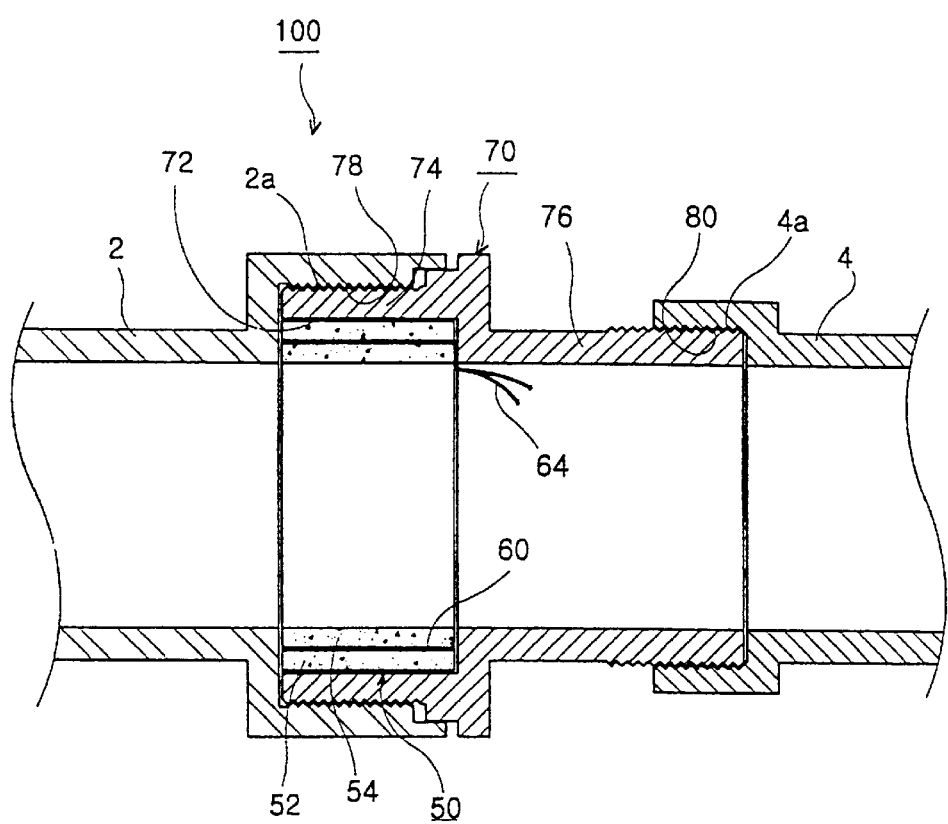
FIG. 5 is a diagram showing the smart foam according to the present invention and the device containing the said smart foam.

FIG. 5 illustrates a device by which the present invention's ring type smart foam may easily be installed in ducts and thus the noise may efficiently be controlled.

The said device (100) includes a holder comprising the first connection part (74) with a hollow (72) for holding the said ring type smart foam (50) inside and the second connection part (76) extended from the said first connection part (74) with a smaller inner diameter than the said hollow (72). Ducts are connected to both ends (the said first connection part (74) and the second connection part (76)) of the said holder (70) and the said ring type smart foam (50) is held (inserted) in the said hollow (72) of the holder (70).

Preferably, the inner diameter of the said ring type smart foam (50) must be the same as that of the second connection part (76) of the said holder (7). More preferably, the inner diameter of the said ring type smart foam (5), the inner diameter of the said holder (70)'s second connection part (76), and the inner diameter of the ducts all must be the same. Such same inner diameter minimizes the irregularity of the flow and irregular changes in the sound field caused by the differences in the cross sectional area of the inside of the ducts and accordingly enables more efficient control.

Additionally, the said holder (70) has screw parts (78)(80) on the circumferences of the first connection part (72) and the second connection part (74) for the connection with ducts (2)(4), to which screw parts, the screw parts (2a)(4a) of the said ducts (2)(4) are connected.

The present invention's device (100) may conveniently be installed upon separating the neighboring ducts and connecting the two ends of the said holder (70) to the separated ducts.

Now, provided below is an explanation of an experiment conducted in order to compare the duct noise control performance of the ring type smart foam of the present invention with that of the conventional plug type smart foam as proposed by Fuller.

<Experiment>

(A) Subject of the Experiment (A)-1. Plug Type Smart Foam

Figure 1:
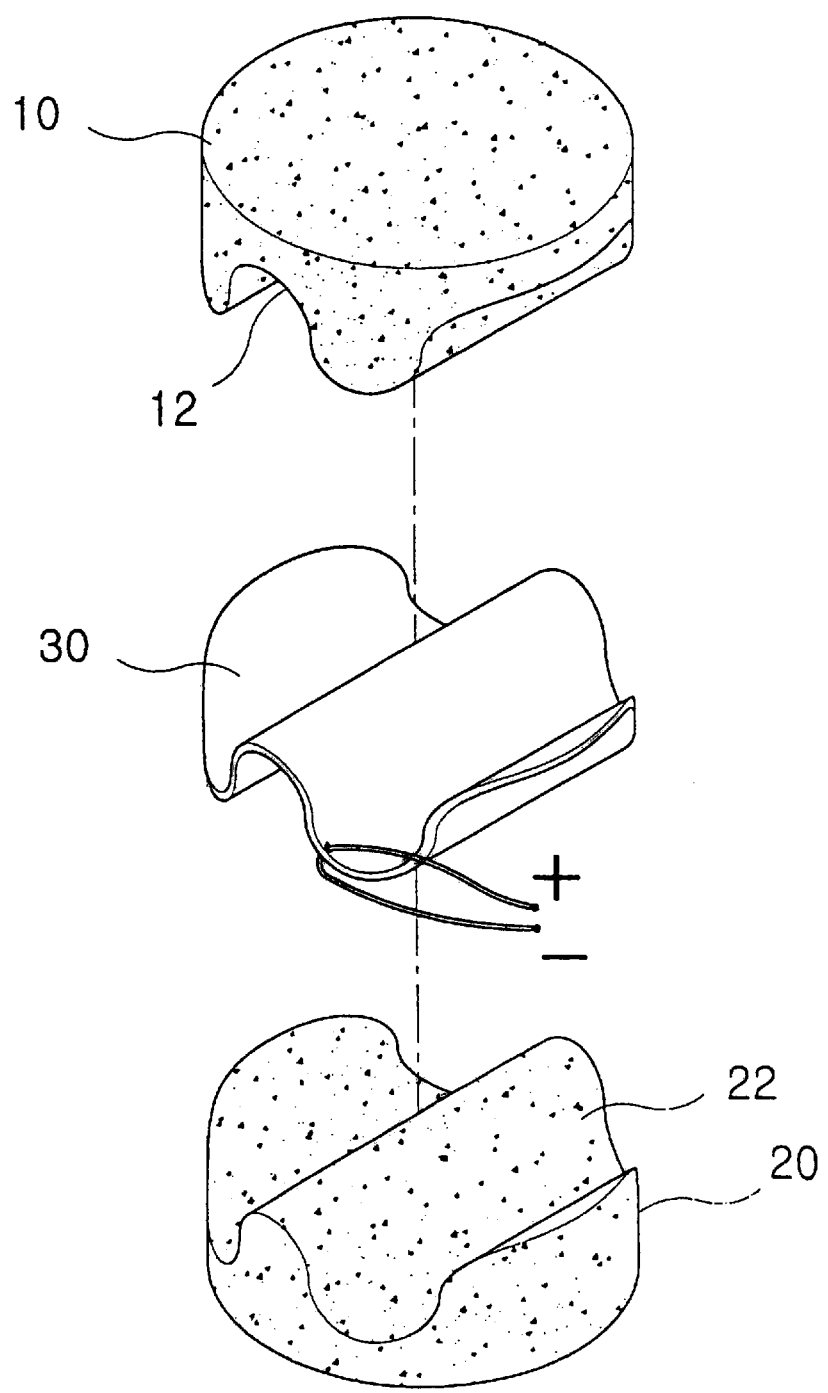
FIG. 1 is a diagram showing the separated conventional plug type smart foam proposed by Fuller.

The plug type smart foam used in this experiment is in the exact form as suggested by Fuller. The overall shape of the plug type smart foam is as illustrated in FIG. 1 and FIG. 2.

For the experiment, the elastic porous polyurethane foam with the diameter of 10 cm and the length of 4 cm was used. The foam was processed to have the continuous semicircular shapes as shown in FIG. 1 and FIG. 2 and a PVDF film was inserted in between the processed foams. In order to maximize the coupling between the foam's solid and the PVDF film, the semi-circles that appear in the foam must be made as large as possible. Accordingly, the radius selected for the semi-circles was approximately 1.3 cm. Additionally, for the purpose of attaining the tolerance to the high voltage applied upon the activation of the actuator, a PVDF film, which was 28 μm thick and on which silver (Ag) was uniformly plated, was selected.

Figure 2:
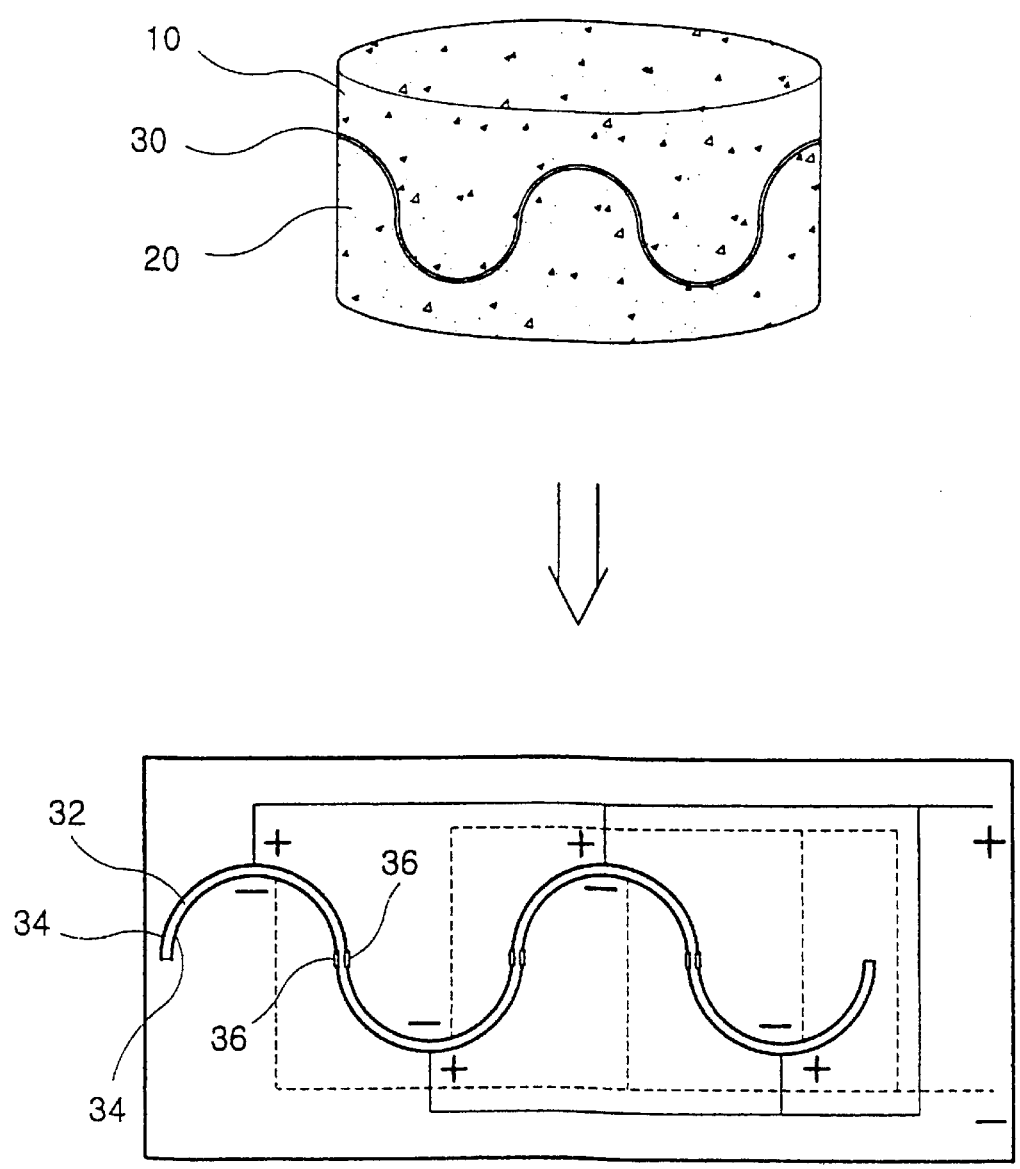
FIG. 2 is a diagram showing the side view of the plug type smart foam proposed by Fuller and the structure of its PVDF actuator.

The shape of the PVDF actuator interposed in between the elastic porous polyurethane foams is as illustrated in FIG. 2. In other words, the silver (Ag) plated on the upper and the lower surfaces of the film (32) was peeled off through the lines (36) in order to electrically insulate the four (4) independent cells on the film. Here, the voltages of the opposite directions were applied to adjacent cells and thus the dipole type sound radiation was prevented. Accordingly, sounds could be efficiently radiated without any cancellation effect. Consequently, the film, installed in the elastic porous polyurethane foam in the continuous semi-circular form, could enable the speaker type sound radiation.

The PVDF film and the electric wires were connected by copper tapes with conductivity, upon which conductive ink was applied for the efficient conveyance of the voltage. The film was fixed using the adhesive in order to prevent the generated sound from being reduced by the absorption into the elastic porous polyurethane foam and in order to facilitate the coupling between the solid of the elastic porous polyurethane foam and the PVDF film.

(A)-2. Ring Type Smart Foam

The ring type smart foam according to the present invention is the smart foam as illustrated in FIG. 3 and FIG. 4. The smart foam, made out of elastic porous polyurethane foam, comprises the external and internal rings (52)(54) and the PVDF film (60). In order to minimize the differences in the cross sectional areas and thus to minimize the resulting changes in the sound field, the ring type smart foam was made to have the internal diameter of 10 cm. The length of the ring type smart foam was 4 cm, which was the same as the length of the above-described plug type smart foam. The outer and inner surfaces of the PVDF actuator were connected to the different electrodes.

(B) Experiment Devices

Figure 6:
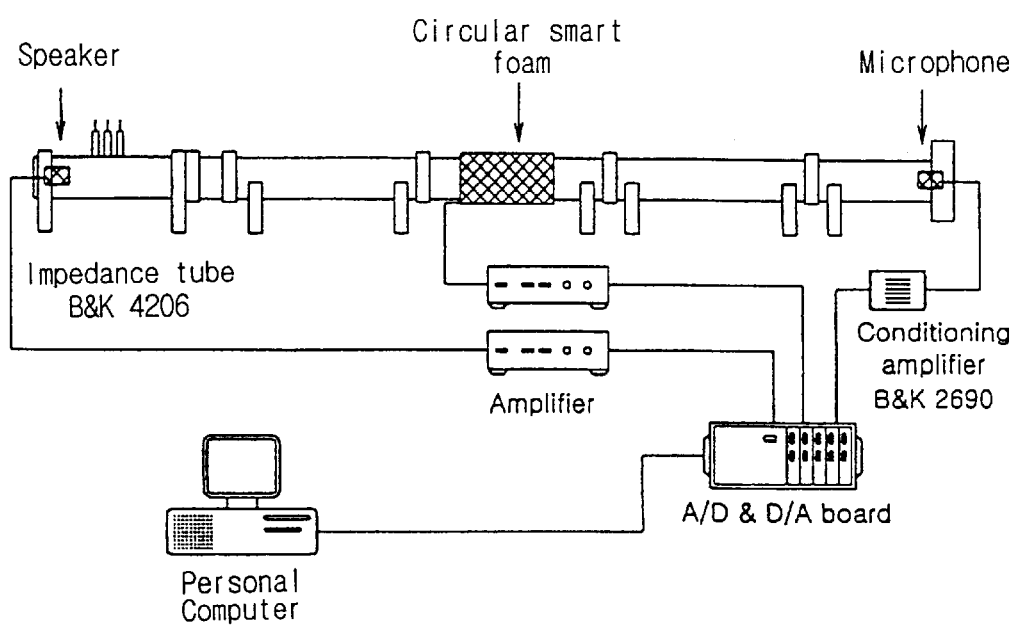
FIG. 6 is a diagram illustrating an experiment device for testing the noise control performance of the smart foam.

The overall structure of the experiment devices is as illustrated in FIG. 6.

The two types of the smart foam described above were located inside of a duct for the noise control. The duct used in the experiment was a ring type duct with the inner diameter of 10 cm, composed of a number of B&K impedance measuring tubes (Type 4206) with the same diameter, the length of which was extended by combining such tubes. The surfaces of the tubes used to extend the length were made smooth to minimize any changes in the sound field caused by the roughness of the surfaces. For the noise control by the ring type smart foam, the sample holder manufactured according to the present invention as illustrated in FIG. 5 was used to install the smart foam in the duct. To minimize the effect of any changes in the cross sectional area, the sample holder with the inner diameter 10 cm was selected. The overall length of the ducts was not affected by the sample holder because the length of the duct was adjusted by appropriate changes in the composition of the tubes. The cut-off frequency of the first higher-order mode of the duct was approximately 1620 Hz and was assumed to be firm acoustically. One end of the duct was closed with a speaker, the original noise source, and the other end was open. The speaker generating the noise was operated within the extent maintaining the linear characteristic and the signal necessary therefor was generated in a personal computer. The distance between the speaker generating the noise and the source of the control sound was 110 cm. An error microphone was located with the distance of 210 cm (the distance between the speaker generating the noise and the error microphone), which was adequately apart from the source of the control sound.

As an experiment for the noise control in ducts, first, the noise control at a single frequency was conducted. However, in most cases, noises are composed of sounds with various frequencies. Thus, for the substantial verification of the performance, the noise control at a certain band of frequencies was also conducted.

The comparison of the control effect in each experiment was made based upon the changes in the power spectrum of the sound pressure measured at the error microphone. First, the power spectrum of the sound pressure was measured at the error microphone only with the original noise activated without any smart foam installed. Then, the sound pressure power spectrum at the error microphone was measured when the control was conducted through the smart foam and, then, was compared with the power spectrum measured without the smart foam. For the ring type smart foam, only the results before and after the control were considered because there are differences in the cross section if no smart foam is installed.

For the noise control in the duct, an adjustment control method using the filtered-x LMS algorithm was applied. The ds1103 board of dSPACE installed in a personal computer was used for the control process. Through such device, the experiment data was collected and the original noise and control signal were generated. No detection microphone was used. Signals received directly from a PC, which were used to generate the control frequencies, were also used as the base signals. In order to implement the filtered-x LMS algorithm, the relationship between the control signals and the control sound signals measured at the error microphone needed to be defined. This is called the cancellation path and was estimated off-line through the LMS method.

(C) Results of the Noise Control Experiment in a Duct Using the Plug Type Smart Foam As explained above, the smart foam in the same structure as the smart foam proposed by Fuller was constructed and was applied for the noise control in a duct. A single frequency and a band of frequencies were generated and the noise control potentiality was estimated at the location of the error microphone.

(C)-1. Result of the Noise Control at a Single Frequency

In order to verify the noise reduction performance of the smart foam, the experiments were conducted both for a low frequency and a high frequency. The low frequency range was from 300 Hz to 400 Hz and the high frequency range was from 750 Hz to 1500 Hz.

Figure 7:
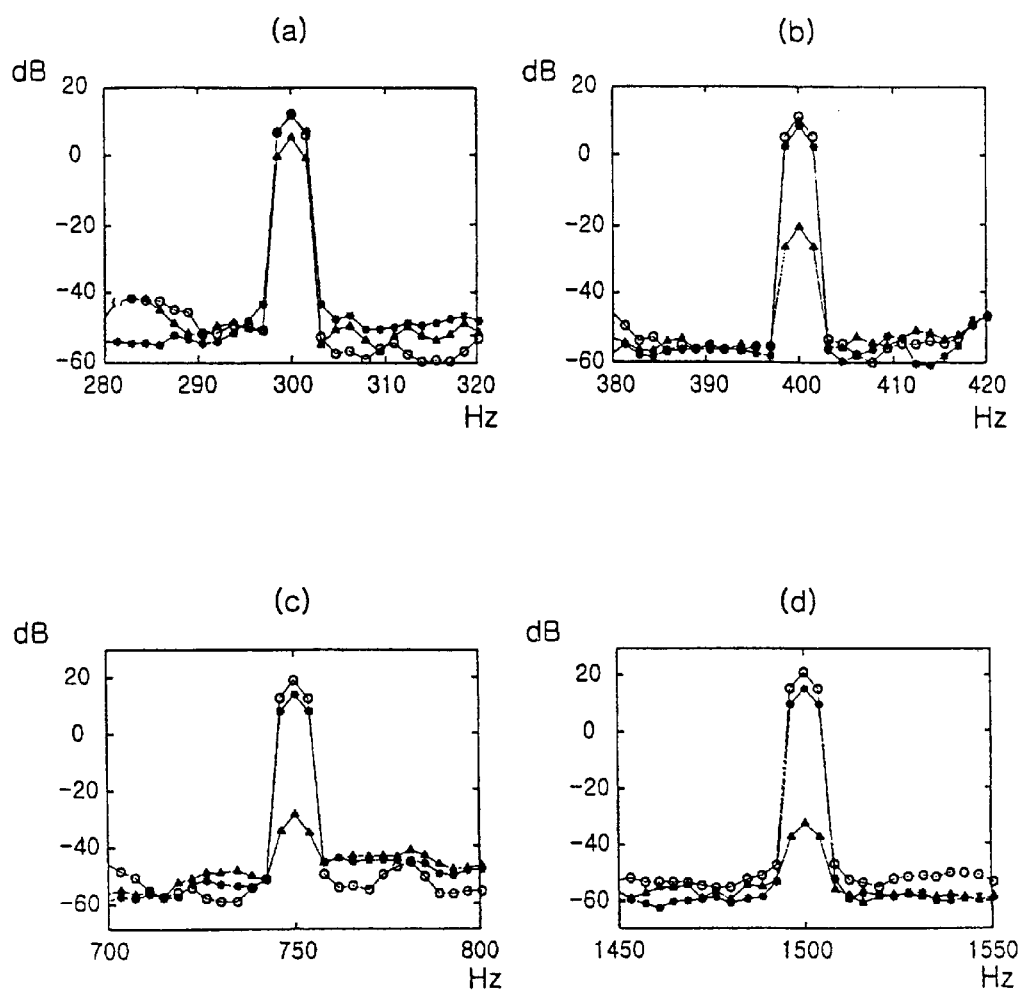
FIG. 7 is a graph showing the result of noise control at a singly frequency, by the conventional plug type smart foam proposed by Fuller.

FIG. 7 illustrates the result of the noise control of the plug type smart foam at a single frequency. The passive noise control merely using the elastic porous foam has hardly shown any effect at a low frequency. In the high frequency range, the noise reduction of approximately 5 dB was achieved. In contrast, the active noise control using the smart foam has accomplished the noise reduction of approximately 10 to 40 dB. As a result, it was verified that the noise at a singly frequency may be controlled through the plug type smart foam.

(C)-2. Result of the Noise Control at a Band of Frequencies

The plug type smart foam's noise control performance at a band of frequencies was tested using the noise with a band of frequencies, the central frequency of which was 600 Hz and the bandwidth of which was 100 Hz, and another band of frequencies, the central frequency of which was 900 Hz and the bandwidth was 200 Hz.

Figure 8:
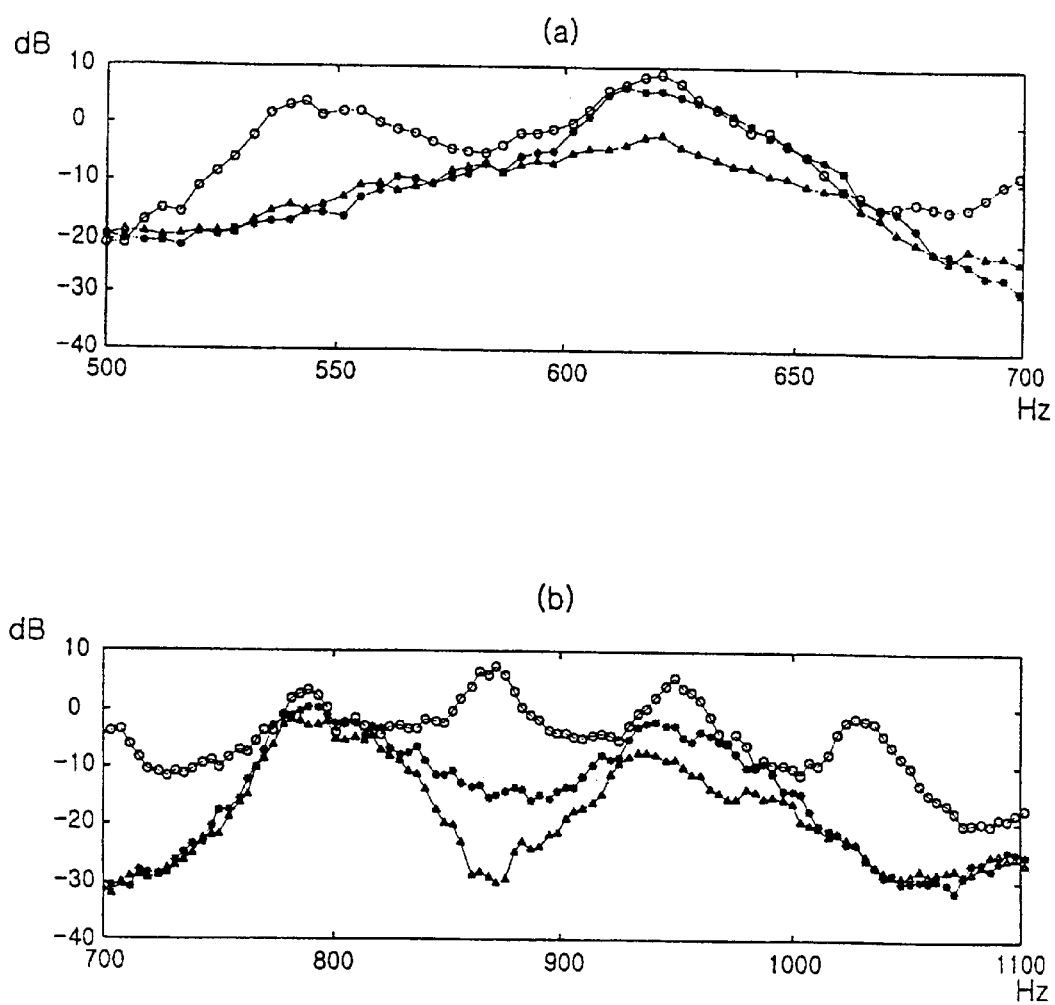
FIG. 8 is a graph showing the result of noise control at frequencies of a certain band, by the conventional plug type smart foam proposed by Fuller.

The result of such noise control is as illustrated in FIG. 8.

The noise control result shows that the noise was reduced around the subject frequencies and the magnitude of the reduction was approximately 10 to 40 dB. Generally, compared with the original noise, the sound pressure was reduced. Even though there were certain points with a little sound pressure increases, such increased level was lower than the original noise level. Thus, the reduction in performance of the active noise control may be disregarded. From the above-described results, it was verified that the active noise control within a duct is possible through the smart foam.

(D) Results of the Noise Control Experiment in a Duct Using the Ring Type Smart Foam In order to test the noise control effect of the smart foam of the present invention proposed for the noise control in a duct with the actual movement of fluid, experiments were conducted with the same conditions as the conditions selected for the above-described plug type smart foam experiment.

In order to create a ring shaped space within the duct, the sample holder specially manufactured as illustrated above was used. The overall length of the duct was kept constant, unaffected by the sample holder inserted to the duct. When the sample holder is installed, there are changes in the cross section of the duct at the portion that the smart foam is located. Thus, it is impossible to measure the exact sound pressure of the original noise. Therefore, for the ring type smart foam, the results of the passive control using the elastic porous foam and of the active noise control using the smart foam were compared to confirm the smart foam's noise control effect in a duct.

(D)-1. Result of the Noise Control at a Single Frequency

Figure 9:
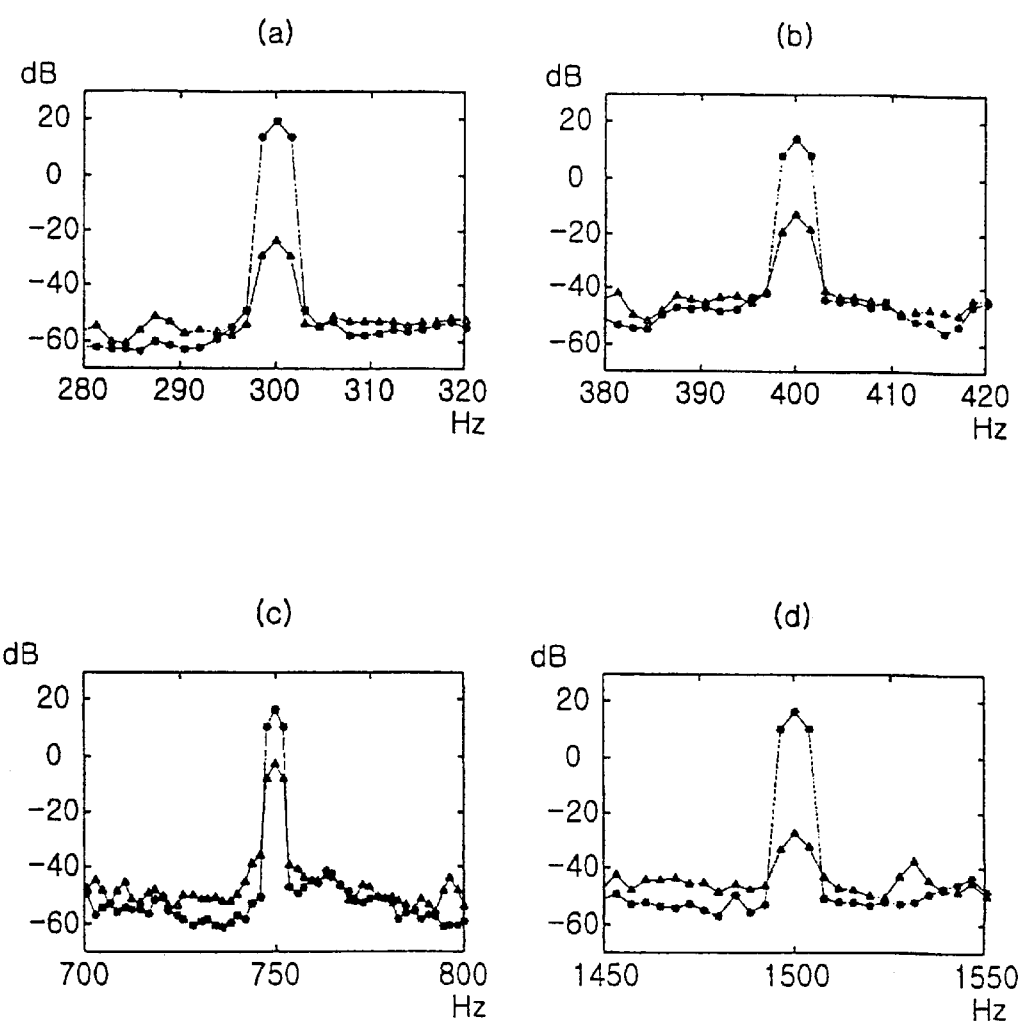
FIG. 9 is a graph showing the result of noise control by the present invention's smart foam at a singly frequency.

FIG. 9 illustrates the result of the ring type smart foam's noise control at a single frequency. Compared with the passive noise control, the active noise control using the ring type smart foam shows the effect of the noise reduction of approximately 20 to 50 dB both in the low frequency and the high frequency ranges. The sound efficiency at a low frequency range of the ring type smart foam was superior to that of the plug type smart foam. Thus, the ring type smart foam demonstrated a greater noise reduction effect at a low frequency level than the plug type smart foam. Furthermore, since the original noise signal was of a single frequency, [the estimation was readily available through an adjustment filter.] Consequently, the result as described above may be obtained. As a system modeling filter, a [300-order] FIR filter was used and as a cancellation path filter, a [50-order] FIR filter was used. Such high-order filters are required because the system modeling filter is affected by changes in the error signal caused by the acoustic reflection (acoustic feedback) at the both ends of the duct and by the changes in the smart foam's impedance caused by the control inputs. The convergent constant was adjusted considering the convergent speed and the stability. Ordinarily, the greater the convergent constant is, the greater the convergent speed is. However, if the value of the constant is too high ($0.1<\mu<1$), the stability of the system may be impaired.

(D)-2. Result of the Noise Control at a Band of Frequencies

For the verification of the ring type smart foam's noise control performance, noise with a band of frequencies, of which the central frequency was 500 Hz and the bandwidth was 100 Hz, and noise with a band of frequencies, of which the central frequency was 900 Hz and the bandwidth was 200 Hz, were used.

Figure 10:
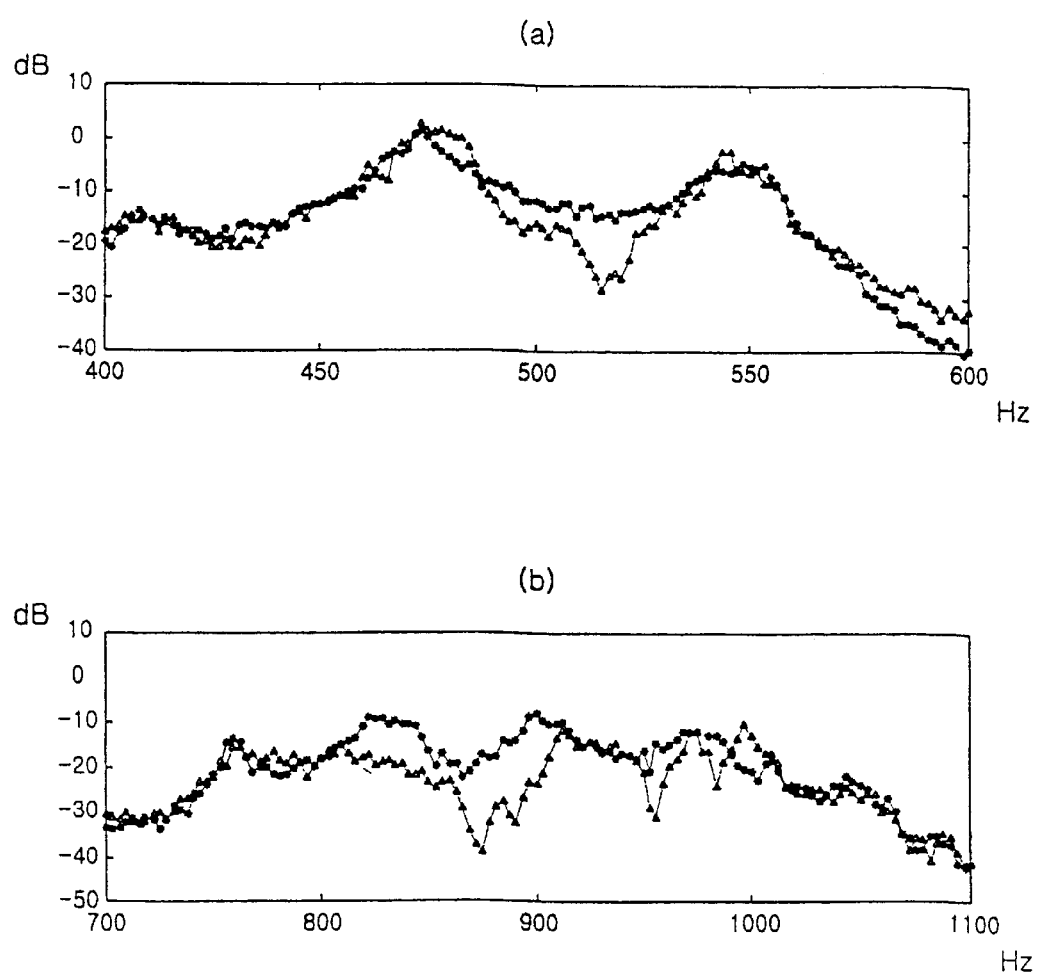
FIG. 10 is a graph showing the result of noise control by the present invention's smart foam at frequencies of a certain band.

The noise control result in this case is as illustrated in FIG. 10.

As with the plug type smart foam's noise control result, the noise was reduced around the subject frequency range. The reduction level was approximately 10 to 20 dB. Since the subject frequency range was a band of frequencies, the estimation therefor was harder than it was in the case of a single frequency. Furthermore, the above-mentioned acoustic feedback and the impedance changes during the smart foam's control process must be taken into account. Thus, in order to adequately reflect these factors, a high-order of the filter needed to be used. However, considering the limitation in the ds1103 board's real-time processing capacity, a 500-order FIR was used as the system modeling filter and a 100-order FIR filter was used as the cancellation path filter for the noise control at a band of frequencies. Therefore, the resulting noise reduction in this case was smaller than it was in the case of a single frequency. In certain local points, the sound pressure was a little higher than it was in the case of passive noise control. Nonetheless, as in the result of the experiment for the plug type smart foam, the increased sound pressure was not as high as that of the original noise. Moreover, the magnitude of the sound pressure increase was smaller than the magnitude of the noise reduction.

As explained above, the present invention may overcome the drawback of the conventional passive noise control of the elastic porous materials by conducting the active and passive noise control within a duct. Particularly, in contrast to the conventional plug type smart foam which blocks the duct and thus may not be used in a duct with the actual movement of fluid, the present invention, by providing the ring type smart foam made out of a ring type elastic porous synthetic resin foam with a PVDF actuator embedded in it, enables the smart foam to be installed in a duct with the actual movement of fluid. Furthermore, the present invention provides an improved noise control performance.

Additionally, through the device composed of the ring type smart foam and a holder according the present invention, the smart foam may easily be installed in a ring type duct. Moreover, because the device does not cause any change or interference in the fluid's movement, an effective noise control becomes possible.

What is claimed is:

1. A device equipped with the ring type smart foam for active noise control in a duct, comprising:

the ring type smart foam (50) composed of an external ring (52) made out of an elastic porous synthetic resin foam material of a certain length, an internal ring (54) made out of an elastic porous synthetic resin foam to be inserted into the said external ring (52), a ring type PVDF film (60) to be interposed between the said external ring (52) and the internal ring (54) for the radiation of sounds, on the outer and inner surfaces of which film conductive material layers are plated, and lead wires (64) connecting the conductive material layers (62) on the outer and inner surfaces of the said PVDF film (60) to different electrodes and conveying voltages thereto in order to enable the PVDF film (60) to radiate sounds: and a holder composed of the first connection part (74) with a hollow (72) for holding the said ring type smart foam (50) inside and the second connection part (76) extended from the said first connection part (74) with a smaller inner diameter than the said hollow (72), to which connection parts (the said first connection part (74) and the second connection part (76)) ducts are connected.

2. The device equipped with the ring type smart foam for active noise control in a duct according to claim 1, wherein the inner diameters of the said ring type smart foam (50) and the second connection part (76) of the said holder (70) are the same.

3. The device equipped with the ring type smart foam for active noise control in a duct according to claim 1, wherein all of the inner diameters of the said ring type smart foam (50), the second connection part (76) of the said holder (70) and the ducts are the same.

4. The device equipped with the ring type smart foam for active noise control in a duct according to any claim from claim 1 to claim 3, further comprising screw parts (78)(80) on the circumferences of the first connection part (72) and the second connection part (74) of the said holder (70) for the connection with ducts.

* * * * *